United States Patent [19]

Walder

[11] Patent Number: 4,598,064

[45] Date of Patent: Jul. 1, 1986

[54] ALPHA-ALPHA CROSS-LINKED HEMOGLOBINS

[75] Inventor: Joseph A. Walder, Iowa City, Iowa

[73] Assignee: University of Iowa Research Foundation, Iowa City, Iowa

[21] Appl. No.: 625,360

[22] Filed: Jun. 27, 1984

[51] Int. Cl.$^4$ .................... A61K 35/14; C07K 13/00
[52] U.S. Cl. ...................................... 514/6; 530/385; 530/405; 530/406; 424/101
[58] Field of Search ............... 260/112.5 R, 112 B, 260/115; 424/101; 514/6

[56] References Cited

U.S. PATENT DOCUMENTS

| | | | |
|---|---|---|---|
| 3,925,344 | 12/1975 | Mazur | 260/112.5 R |
| 4,001,200 | 1/1977 | Bonsen et al. | 260/112 B X |
| 4,001,401 | 1/1977 | Bonsen et al. | 424/101 X |
| 4,053,590 | 10/1977 | Bonsen et al. | 260/112 B X |
| 4,061,736 | 12/1977 | Morris et al. | 514/6 |
| 4,136,093 | 1/1979 | Bonhard et al. | 260/112 B X |
| 4,301,144 | 11/1981 | Iwashita et al. | 260/112 R X |
| 4,336,248 | 6/1982 | Bonhard et al. | 424/101 |
| 4,376,059 | 3/1983 | Davis et al. | 252/316 |
| 4,377,512 | 3/1983 | Ajisaka et al. | 260/112 B |
| 4,401,652 | 8/1983 | Simmonds et al. | 424/101 |
| 4,473,494 | 9/1984 | Tye | 260/112 B |
| 4,473,496 | 9/1984 | Scannon | 260/112 B |
| 4,529,719 | 7/1985 | Tye | 514/6 |

OTHER PUBLICATIONS

Biochemistry, 11 No. 19 (1972), 3576–3582, Benesch et al.
Biochem-Biophys. Res. Communications, 63, No. 4 (1975), 1123–1129, Benesch et al.
Fed. Proc. 34, No. 6, (1975), 1458–1460, Mok et al.
Walder, et al., J. Mol. Biol. (1980) 141, 195–216, "Development of Antisickling Compounds that Chemically Modify Hemoglobin S Specifically within the 2,3-Diphosphoglycerate Binding Site".
1982 FASEB Abstract Form.
R. W. Tye, et al., Advances in Blood Substitute Research (1983) pp. 41–49, "Modification of Hemoglobin—Tetrameric Stabilization".
Fronticelli et al., Advances in Blood Substitute Research (1983) pp. 51–57, "Neohemoglobins as Blood Substitutes".

Primary Examiner—Howard E. Schain
Attorney, Agent, or Firm—Zarley, McKee, Thomte, Voorhees & Sease

[57] ABSTRACT

Blood substitute and blood plasma expanders comprising alpha-alpha cross-linked stroma-free hemoglobin, which is substantially free of hemoglobin derivatives modified at other sites. The hemoglobin composition is intramolecularly cross-linked between Lys 99 Alpha$_1$ and Lys 99 Alpha$_2$.

11 Claims, 3 Drawing Figures

ALPHA-ALPHA CROSS-LINKED HEMOGLOBINS

BACKGROUND OF THE INVENTION

This invention relates to a modified hemoglobin composition, used as a blood substitute and a blood plasma expander. There is a critical need within the medical industry for blood substitutes and blood volume expanders. This need occurs not only because of the shortage of donor blood in bloodbanks, but also because of many problems that commonly exist with donor bloodbank practices. For example, there is an increasingly significant risk of disease transmission such as acquired immunodeficiency syndrome, commonly referred to as "AIDS", and even much more commonly, a real hepatitis risk. The shelf life of whole blood is also relatively short, not usually lasting longer than 30 days. There is also the problem of the need for blood typing, etc. with donated whole blood samples.

Accordingly, there is a very real and continuing need which has existed for some time, for blood substitutes or blood plasma expanders which can be conveniently prepared from a base hemoglobin source, such as discarded blood samples. This invention has as its primary objective, the fulfillment of this continuing need.

Currently there are two available possible routes for blood substitutes and blood plasma expanders which are being investigated. The first is fluorocarbons and the second is modified hemoglobins. The modified polyhemoglobins are represented by U.S. Pat. No. 4,001,401. Fluorocarbons are also receiving much active investigation at the present. However, it is believed unlikely that fluorocarbons will ever successfully take over the market for blood substitutes or blood plasma expanders because these are known to at times block the natural immune system. In addition, the use of fluorocarbons is limited to situations in which high partial pressures of oxygen can be administered. They do not have a sufficiently high oxygen binding capacity for use under normal environmental conditions. Thus, while currently available materials do represent a contribution and some advancement in medical sciences directed towards the concept of a blood substitute and blood plasma expander, there is currently nothing of significant commercial affect available on the market.

There is also the problem of not only developing an effective oxygen carrying blood substitute which will effectively release the oxygen for body use, but also developing a composition which will not be renally eliminated. A natural mammalian hemoglobin is a tetramer, which in plasma will in the oxy form have a tendency to split into two alpha-beta dimers, each having a molecular weight of approximately 32,000. These dimers are small enough to be filtered by the kidneys and be excreted, with the result being a potential for renal injury and a substantially decreased intravascular retention time.

It therefore becomes readily apparent that there is a continuing need for a therapeutic product useful as a blood substitute and blood plasma expander, which will effectively bind oxygen, but not bind it so tightly that it will *not* be released for body use; and, for development of a product which will not split into alpha-beta dimers, capable of rapid elimination by the renal route as well as loss from the circulation through capillary beds in other tissues.

Accordingly, another primary object of the present invention is to prepare an effective blood substitute and blood plasma expander from modified hemoglobin.

Another objective of the present invention is to prepare a blood substitute and blood plasma expander based on a derivative of hemoglobin cross-linked specifically between the alpha chains.

Yet another object of the present invention is to prepare an effective modified hemoglobin which has a relatively low oxygen affinity, that is, will release the oxygen easily for body use, but which at the same time is incapable of being split into alpha-beta dimers and as a result, rapid renal elimination is prevented.

Yet another objective of the present invention is to prepare a modified hemoglobin, cross-linked between the alpha chains at specifically Lys 99 Alpha$_1$ to Lys 99 Alpha$_2$.

Yet another objective of the present invention is to prepare an even further modified hemoglobin, which is not only alpha-alpha cross-linked but one which is also selectively modified with an acylating agent at the 2,3-diphosphoglycerate binding site, located between the beta chains, to introduce a negatively charged group within this region which even further enhances hemoglobin oxygen release, making the cross-linked composition even more effective in certain applications. Such derivatives having a markedly reduced oxygen affinity may be particularly useful, for example, in the treatment of ischemia (i.e., heart attacks and strokes) as well as in the replacement of blood loss.

A still further objective of the invention is to provide a blood substitute and plasma expander that is readily available, stable under prolonged storage, and which can be used without significant disease transmission risk.

A yet further objective of the present invention is to provide an alpha-alpha cross-linked modified hemoglobin having a molecular weight of approximately 64,000, which will not split into dimers of about 32,000 molecular weight, during use.

A still further objective of the present invention is to provide a cross-linked hemoglobin, which is alpha-alpha cross-linked, and substantially free of hemoglobins modified at other sites, thus diminishing the risk of antigenic reaction which can occur with random modifications of hemoglobin.

SUMMARY OF THE INVENTION

Figure 1:
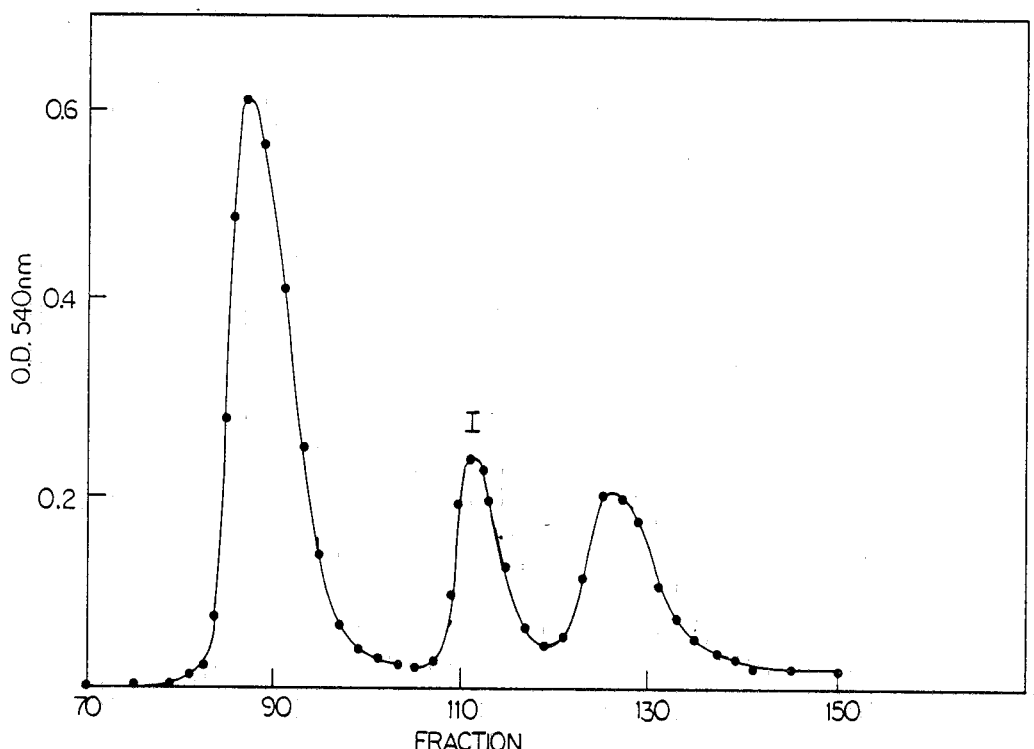
FIG. 1 is an elution profile monitored by the optical density at 540 nm for the purification of the alpha-alpha cross-linked derivative by chromatography on a DEAE (diethylaminoethyl) cellulose column.

A new hemoglobin composition, which is intramolecularly cross-linked between Lys 99 Alpha$_1$ and Lys 99 Alpha$_2$, and blood substitutes and blood plasma expanders comprising a therapeutically effective amount of the cross-linked hemoglobin, soluble and aqueous in physiological fluids and capable of reversibly binding oxygen, coupled with a pharmaceutically acceptable carrier. In an additional preferred embodiment for certain conditions, further modification occurs at the 2,3-diphosphoglycerate binding site by a second reagent such as mono(3,5-dibromosalicyl) fumarate which introduces a negatively charged group at this position.

DETAILED DESCRIPTION OF THE INVENTION

Normal hemoglobin useful in animals is a tetramer, commonly referred to by the symbol Hb4. The tetramer has a molecular weight of about 64,000 and is comprised of four polypeptide chains, two identical alpha chains and two identical beta chains noncovalently linked together. The tetramer Hb4, under oxygenated conditions, readily dissociates into two alpha-beta dimers. Dissociation of the tetramer into alpha-alpha and beta-beta dimers, or alpha and beta monomers does not occur to any significant extent under physiological conditions. With regard to modifying hemoglobin such that it has a beta-beta intramolecular cross-link, see a previously published article, Walder, et al., *Journal of Molecular Biology* (1980), 141, 195–216. The referenced article deals with selectively cross-linking oxyhemoglobin at the beta chains of the tetramer, between Lys 82 Beta$_1$ and Lys 82 Beta$_2$ with bifunctional acylating agents and the potential use of this modification in the treatment of sickle cell disease. The cross-link is advantageous in that it markedly increases the solubility of sickle cell hemoglobin (hemoglobin S) in the deoxygenated form while having relatively litle effect on the intrinsic oxygen binding properties of hemoglobin. In another article, a second derivative cross-linked between the beta chains with the same reagents as reported by Walder, was prepared and tested as a blood substitute, Tye et al. (1983) *Advances in Blood Substitute Research* (Bolin, R.B.; Geyer, R.P. and Nemo, G.J. eds), pp. 41–49, Alan R. Loss, New York.

Surprisingly, in accordance with the present invention, it has been discovered that deoxyhemoglobin can be cross-linked selectively at a novel site between the alpha chains of the tetramer. The site of cross-linking has been established by x-ray crystallographic studies to be from Lys 99 Alpha$_1$ to Lys 99 Alpha$_2$. The result is a molecule which will not dimerize, and a molecule whose oxygen binding properties are improved, that is, the oxygen affinity is decreased, if compared to that of unmodified natural hemoglobin.

It is important to this invention and to an appreciation of its contribution, to recognize that in the derivative of hemoglobin described the cross-linking occurs intramolecularly and at a specific site on the hemoglobin molecule, from Lys 99 of one alpha chain to Lys 99 of the second alpha chain. This is distinctly different from random cross-linking. It is a specific *intra* molecular cross-link, as opposed to both *inter* and *intra* molecular cross-linking occurring in a random fashion as in Bonsen, U.S. Pat. No. 4,001,401. Previous studies, Bunn, et al., *Journal of Experimental Medicine*, (1969), 129, 909–924, had shown that hemoglobin is filtered from the circulation by the kidney as alpha-beta dimers, and that derivatives of hemoglobin that are cross-linked so as to inhibit the dissociation of the tetramer have a decreased filtration rate, and prolonged intravascular retention time, and hence may be useful as a blood substitute. For this purpose, Bonsen et al. have described the use of a number of known nonspecific cross-linking agents which react with hemoglobin nonselectively, potentially at as many as 40–50 different sites on the hemoglobin molecule. In contrast, the cross-linked hemoglobin decribed in this invention is a specific derivative cross-linked at a unique site on the hemoglobin molecule, Lys 99 Alpha$_1$ to Lys 99 Alpha$_2$. The advantages of this composition as a blood substitute are described in the following paragraphs.

Where the cross-linking reagent reacts with hemoglobin in a nonselective fashion, the mixture of reaction products would include, in addition to derivatives which are intramolecularly cross-linked, substantial amounts of hemoglobin, both modified and unmodified, that is not cross-linked, as well as higher molecular weight aggregates due to intermolecular cross-linking between hemoglobin tetramers. In Bonsen, et al., this entire mixture, without further fractionation constitutes the cross-linked hemoglobin composition of the product. For a therapeutically useful product, it would probably be essential to at least remove the non-cross-linked hemoglobin which can dissociate into alpha-beta dimers capable of filtration by the kidney, and hence poses the risk of renal injury. Even the isolation of higher molecular weight aggregates of polymerized hemoglobin due to intermolecular cross-linking may not be sufficient for this purpose since in this case, it is still possible for an alpha-beta dimer to split out and dissociate from the complex as in the following schematic:

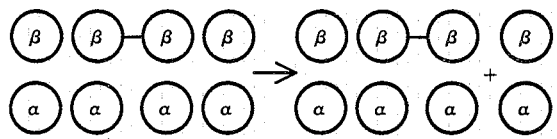

Such is not possible with the alpha-alpha cross-linked hemoglobin composition of the present invention in which cross-linking occurs intramolecularly. The alpha-alpha cross-linked hemoglobin may, of course, be used as the substrate for further intermolecular cross-linking should it prove that higher molecular weight aggregates of polymerized hemoglobin are clinically useful.

Even with attempts to isolate a particular molecular weight fraction from the reaction mixture, where the cross-linking reagent reacts nonselectively with hemoglobin, the final product would still in general contain a mixture of hemoglobin derivatives that are modified at a number of different sites on the molecule. This random modification increases the risk of antigenic reaction to the foreign protein. With a single specific site of modification as in the alpha-alpha cross-linked derivative of the present invention, this risk is decreased. This is particularly true in this case since the site of cross-linking, Lys 99 Alpha$_1$ to Lys 99 Alpha$_2$, is at a relatively inaccessible region of the molecule near the center of the hemoglobin tetramer.

In a preferred embodiment of the present invention, for certain applications such as ischemia, an even further modification of the alpha-alpha cross-linked derivative occurs with a second reagent which introduces a negatively charged group at the 2,3-diphosphoglycerate binding site between the beta chains, with the result being a further enhanced capability for oxygen release. In the derivatives cross-linked between the beta chains described above, the site of cross-linking is located within the 2,3-diphosphoglycerate binding site potentially precluding or inhibiting further modifications within this region.

The method of obtaining the starting material for the polymerization, that is, stroma-free hemoglobin represents state of the art knowledge. It is known how hemoglobin is separated from cells, including isolating it in substantially free form from cellular debris and stroma. For example, hemoglobin to be modified in accordance with this invention can be isolated from discarded blood samples, whose shelf life has exceeded ordinarily regarded safe limits. For details of a suitable isolation technique, see for example, U.S. Pat. No. 4,001,401, at column 4, line 49 through column 5, line 13, which is incorporated herein by reference. In addition, see Rabiner, et al., *Journal of Experimental Medicine* (1967), 126, 1127–1142; and Feola, et al., *Surgery Gynecology and Obstetrics* (1983), 157, 399–408, which are also incorporated herein by reference. As in Feola's work, the source of hemoglobin may be other species, for example, bovine or porcine hemoglobins. Bacterial strains engineered to produce hemoglobins by recombinant DNA techniques may also be used as the source of hemoglobin.

The isolated hemoglobin $Hb_4$ is now ready for modification and treatment and cross-linking in accordance with the present invention. It is essential for the desired alpha-alpha cross-linking reaction to occur, that the hemoglobin for reaction be deoxygenated. If the hemoglobin is oxygenated, cross-linking will occur between the beta chains, in accordance with the references cited above. Deoxygenation is accomplished by extensively purging the stroma-free hemoglobin prior to cross-linking with inert gases such as nitrogen or argon. Deoxygenation is essential to render the reactive site at Lys 99 of the alpha chains accessible to the cross-linking reagent. In oxyhemoglobin the conformation is such that this region of the molecule is totally inaccessible.

It has been mentioned that the reaction can be controlled to assure deoxygenation by purging with argon or nitrogen or other inert gases. However, alternatively, or in combination, deoxygenation may be achieved by reaction with sodium dithionite or other conventional reducing agents, such as ferrous citrate. Deoxygenation by purging under a blanket of appropriate inert gas should occur for from about one hour to about three hours, at normal atmospheric pressure at a temperature of from about 0° C. to about 40° C. Purging for a time within this framework assures that deoxygenation will have occurred, making accessible the site of cross-linking between the alpha chains, Lys 99 Alpha$_1$ to Lys 99 Alpha$_2$. After purging, the composition is now ready for reaction with the cross-linking reagent.

The cross-linking agent employed must react with a substantial degree of specificity at Lys 99 of the alpha chains in deoxyhemoglobin. The reaction with the cross-linking agent to form a stable covalent adduct occurs at the -amino group of the side chain of the lysine residue. There are 42 other lysine residues and the amino terminal amino groups of the four polypeptide chains of hemoglobin at which competing reactions may occur. The general formula of suitable cross-linkers which may be employed is:

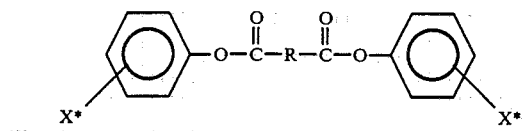

*X can be any organic moiety attached to the ring.

This preferred formula represents phenyl esters which are effective cross-linkers. An important fact is that the cross-link bridge

is formed. This is the cross-link bridge which links the amino groups of the two lysine residues, i.e.,

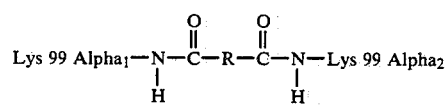

Substitution of groups on the cross-link bridge may affect the properties of the modified derivative, as well as the reactivity of the compound. It is known that R may vary in length, and could, for example, be $C_2H_4$, $C_3H_6$, or an unsaturated chain. Generally R can be any organic moiety, whether substituted or unsubstituted of chain lengths varying from 2 to about 8. R may also be substituted with a specific functional group such as carboxyl group in which case the additional carboxyl group would become attached to the hemoglobin molecule on the cross-link bridge. The functional group that reacts with the amino group of the lysine residue is:

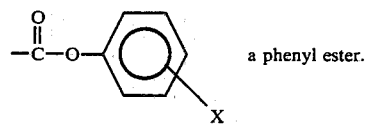 a phenyl ester.

Other possibilities for reaction at amino groups include:

 an aliphatic ester;

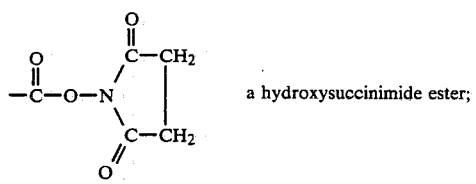 a hydroxysuccinimide ester;

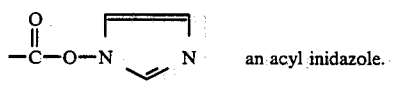 an acyl inidazole.

All of these can be thought of as acylating agents. In addition, the reactive group may also be an imidoester:

or a related amidinating reagent, or a sulfonyl halide. It is possible that certain dialdehydes may also be used to cross-link the two Lys 99 Alpha residues by formation of a Shiff's base and reduction with sodium borohydride or sodium cyanoborohydride carried out to convert the Shiff's base to an amine linkage as in the following equation:

Alkyl halides, or sulfonate esters or other alkylating agents may also be used to cross-link the amino groups of the lysine residues.

The most preferred cross-linking agent is bis(3,5-dibromosalicyl) fumarate. It will effectively cross-link the two Lys 99 Alpha residues in accordance with the following schematic:

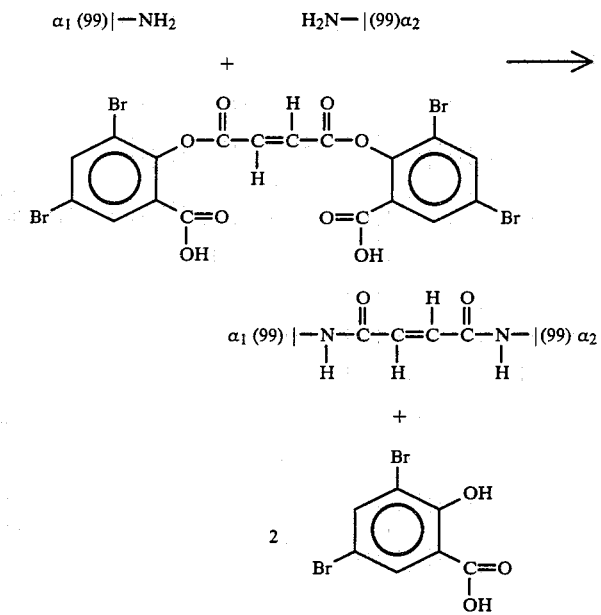

The reaction with the cross-linking agent and the deoxygenated hemoglobin can occur at a temperature of from about 4° C. to about 45° C., preferably from about 25° C. to about 40° C. The pH of the reaction can vary from about 5.5 to about 10, preferably from about 6 to about 8, with the reaction occurring in an aqueous solution of salts, typically having an ionic strength of 0.2 molar Bis-Tris buffer in a molar salt solution up to a concentration of about one molar. The ratio of cross-linking agent to hemoglobin can be from about 1:1 to about 10:1, preferably 1.5:1 to about 4:1. One may, in other words, use up to a tenfold excess of cross-linking agent to assure completion of cross-linking. The time for the reaction again will vary, but can be up to two hours for a sufficient cross-linking to have occurred.

The cross-linked derivative can be separated from the unreacted hemoglobin and impurities modified at other sites by ion exchange chromatography, gel filtration, and other chromatographic techniques. Chromatographic procedures using high pressure liquid chromatography may also be used. In certain cases, it may be possible to sufficiently purify the cross-linked derivative by non-chromatographic methods such as ultrafiltration.

The hemoglobin is now cross-linked at the Lys 99 Alpha$_1$ to Lys 99 Alpha$_2$ position, and may be used as is, as an effective blood substitute, it having been found to have a low oxygen affinity and suitable oxygen release, and having also been found resistant to dimerization and hence rapid removal from the circulation by renal elimination.

For parental use, the purified derivative can be dialyzed or exchanged by ultrafiltration into a physiological saline solution at a pH of 7.4 and concentrated to approximately 7% (7g hemoglobin per 100 milliliter). The material, of course, must be substantially endotoxin free and packaged under sterile conditions. It may also be possible to store the hemoglobin as a lypholyzed powder which would be reconstituted when needed by the addition of saline.

The cross-linked modified hemoglobin, cross-linked as heretofore discussed intramolecularly between Lys 99 Alpha$_1$ and Lys 99 Alpha$_2$ can be used as is, for a blood substitute and blood plasma expander, as a pharmaceutical composition with an acceptable carrier, and with other plasma substitutes and plasma expanders. The pharmaceutical carriers can be crystaloids, including physiological saline, a mixture consisting of saline and glucose, Ringer's solution, lactated Ringer's solution, Locke-Ringer's solution, Krebs-Ringer's solution, Hartmann's balanced saline, and heparinized sodium-citrate-citric acid-dextrose solution.

The cross-linked hemoglobin can be mixed with water soluble physiologically acceptable polymeric plasma substitutes such as poly(ethylene oxide), polyvinylpyrolidone, polyvinyl alcohol, and ethylene oxide-polypropylene glycol condensates. Additionally, it can be mixed with colloidal-like plasma substitutes and plasma expanders such as linear polysaccharides, including dextrans, albumin, other plasma proteins, pectins, balanced fluid gelatin and hydroxyethyl starch. Generally, the pharmaceutical compositions will contain about 1% to about 10% by weight of the modified hemoglobin admixed with one of the above carriers, or a mixture thereof. Conventional methods for administering the therapeutic agents are known medical state of the art, see for example, Tares and King (1980) in Remington's Pharmaceutical Sciences, (Osol, A. ed.) pp. 1488-1497, Mack Publishing Company, Easton, Pa., which is incorporated herein by reference.

As heretofore mentioned an additional important advantage of the Lys 99 Alpha$_1$ to Lys 99 Alpha$_2$ cross-linked hemoglobin is that the 2,3-diphosphoglycerate binding site is still accessible for further modification with other reagents. It has also been found, and is therefore preferred in certain circumstances such as ischemia, with respect to the intramolecular cross-linked hemoglobin of the present invention, that the attachment of a negatively charged group within this region will act as a permanently bound anion and decrease the oxygen affinity of the hemoglobin. This is, of course, desirable since it means that the hemoglobin will more easily release its oxygen for use by the tissues.

In principle, a number of different derivatives could be prepared with a range of oxygen affinities, depending on the attached group, for different applications. Hemoglobin derivatives having a very low oxygen affinity may be particularly useful in the treatment of ischemia (heart attacks and strokes), for example. Even for simple blood replacement, it may be beneficial to have an oxygen affinity lower than that produced by the alpha chain cross-link alone.

Pyridoxal phosphate and other aldehyde derivatives have been used previously to introduce negatively charged groups within the 2,3-diphosphoglycerate binding site, Benesch, et al., *Biochemistry*, (1972), 11, 3576-3582. These compounds react with deoxyhemoglobin and require reductive alkylation for permanent covalent attachment. The compounds described here react with oxyhemoglobin, and hence do not require deoxygenation of the sample, nor is any further reaction, such as reductive alkylation, required to give the final derivative.

The prototype of these compounds and the one most preferred is mono(3,5-dibromosalicyl) fumarate. This compound reacts selectively with oxyhemoglobin at lysine 82 beta and introduces a negatively charged carboxylate group within the 2,3-diphosphoglycerate (DPG) binding site.

The following examples are offered to further illustrate, but not limit, the process, product and medical techniques of the invention.

EXAMPLE 1

The Reaction of Bis(3,5-Dibromosalicyl) Fumarate with Deoxyhemoglobin and Isolation of the Derivative Cross-Linked between the Alpha Chains A solution of hemoglobin is prepared at a concentration of 2.0 mM in 0.2M Bis-Tris buffer at pH 7.2. The hemoglobin is initially in the oxy form. Oxygen is removed by purging with argon or nitrogen, or alternatively by reaction with sodium dithionite or some other reducing agent. A solution of bis(3,5-dibromosalicyl) fumarate at a concentration of 3.0 mM is prepared in the same buffer as hemoglobin and deoxygenated with a nitrogen purge. To the hemoglobin solution is added an equal volume of the solution of bis(3,5-dibromosalicyl) fumarate and the reaction allowed to proceed for two hours at 37° C. The final concentration of hemoglobin and the compound are 1.0 mM and 1.5 mM, respectively. Under these conditions, the yield of the derivative cross-linked between the alpha chains at Lys 99 Alpha$_1$ to Lys 99 Alpha$_2$ is 10-20%. At the end of the reaction, glycine is added to a final concentration of 0.1M to consume any remaining amount of the cross-linking reagent and prevent further reaction with hemoglobin which may occur during the isolation of the cross-linked derivative.

After the reaction the hemoglobin solution is dialyzed against 0.2M glycine buffer at pH 7.8 or exchanged with the glycine buffer by ultrafiltration. In this step the hemoglobin becomes oxygenated. The cross-linked derivative is then separated from unreacted hemoglobin and impurities due to modifications at other sites by chromatography on DEAE cellulose. The column is initially equilibrated with 0.2M glycine buffer at pH 7.8. After application of the hemoglobin, the sample is eluted from the column with a 0.03 to 0.06M NaCl gradient in the same buffer. The elution profile is shown in FIG. 1. The first peak at fraction 90 is unmodified hemoglobin. The peak at fraction 110 (I) is the desired alpha-alpha cross-linked derivative. The third peak at fraction 128 is a mixture of derivatives modified at other sites and includes derivatives cross-linked between the beta chains. Minor remaining non-cross-linked impurities (<5%) coeluting with the alpha-alpha cross-linked derivative can be removed by gel filtration in the presence of 1M MgCl$_2$. An improved purification in the first step may be obtained by high pressure liquid chromatography using a DEAE or QAE (quaternary aminoethyl) column.

The yield of the isolated alpha-alpha cross-linked derivative in the example shown in FIG. 1 was approximately 15%. Since most of the remaining material is unmodified hemoglobin, the yield may be substantially improved by increasing the concentration of the reagent and the reaction time. Also, the unmodified hemoglobin may be recovered and reacted further with the cross-linking reagent.

Figure 2:
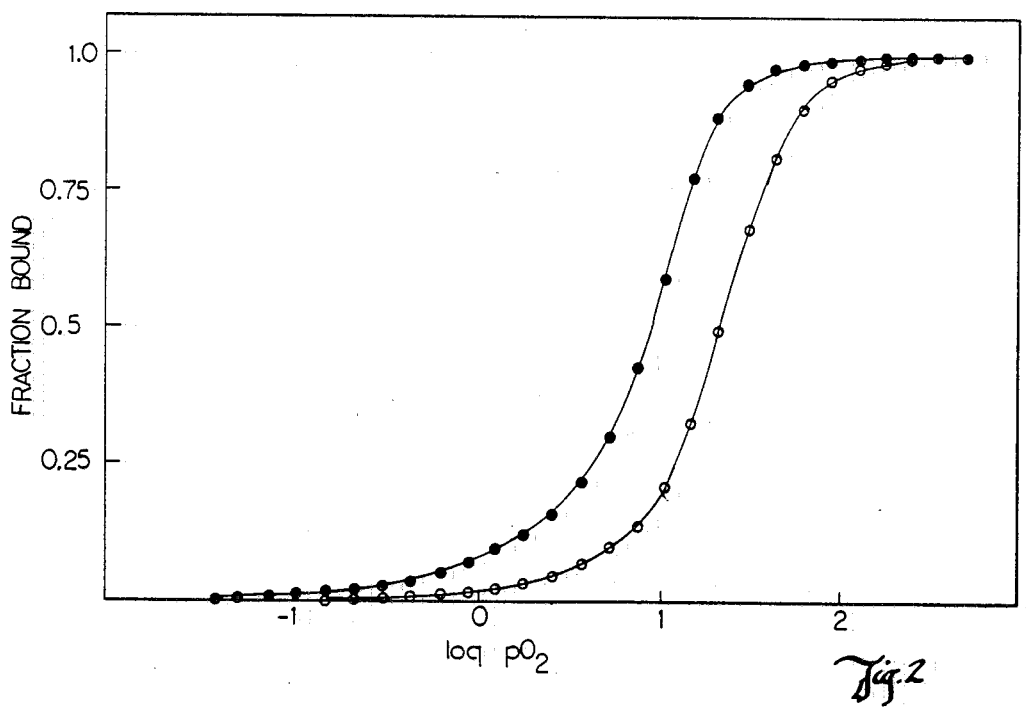
FIG. 2 is an oxygen equilibrium curve showing the fraction of oxygen bound as a function of the log of the partial pressure of oxygen, for both normal adult hemoglobin (closed circles) and the alpha-alpha cross-linked derivative (Lys 99 Alpha$_1$-Lys 99 Alpha$_2$) (open circles).

FIG. 2 illustrates the oxygen equilibrium curve of the alpha-alpha cross-linked derivative prepared as described above. The oxygen equilibrium curve is plotted as the fraction of oxygen bound as a function of the log of the partial pressure of oxygen. In the graph the closed circles represent normal adult human hemoglobin and the open circles, the cross-linked derivative (Lys 99 Alpha$_1$ to Lys 99 Alpha$_2$) The conditions were 0.05M Bis-Tris buffer pH 7.0 with 0.1M NaCl at 25° C. The concentration of hemoglobin in both cases was 0.2 mM. Under these conditions the P$_{50}$ (the partial pressure of oxygen at which half-saturation of the hemoglobin occurs) for native hemoglobin was 6.3 mM Hg and for the cross-linked derivative 15.1 mm Hg. The right shift in the oxygen binding curve for the alpha-alpha cross-linked derivative (i.e., a greater P$_{50}$) indicates a decrease in the oxygen affinity. Correspondingly, the release of oxygen from the cross-linked derivative is greater than from unmodified hemoglobin at higher partial pressures of oxygen. The cooperativity of the cross-linked derivative is not substantially decreased. The Hill coefficient determined in the experiments shown for the cross-linked derivative was 2.2.

Figure 3:
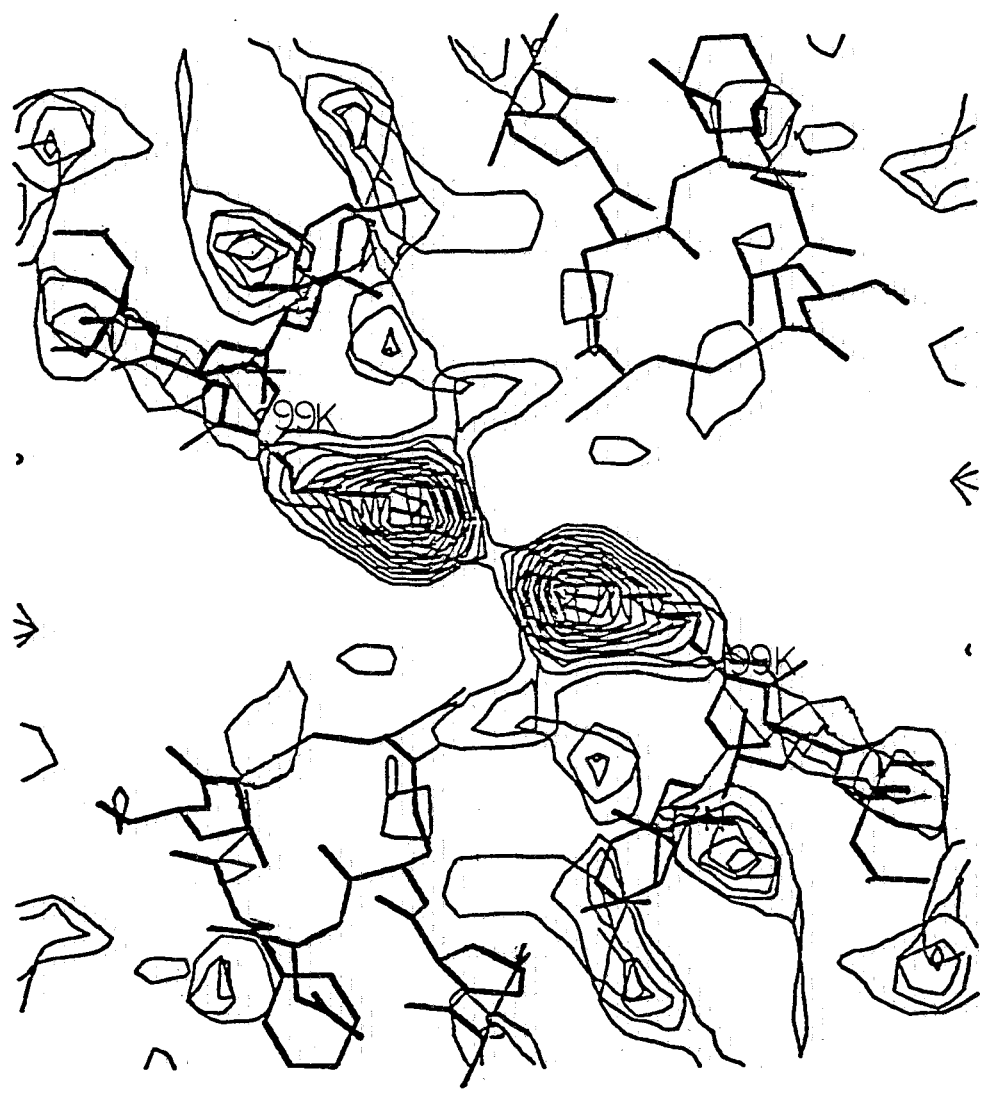
FIG. 3 is the difference electron density contour map between the alpha-alpha cross-linked derivative and native deoxyhemoglobin superimposed upon the atomic model of hemoglobin in the region of the cross-link.

Two-dimensional gel electrophoresis of the cross-linked derivative and amino acid analysis of the isolated cross-linked polypeptide chains first established that the site of the cross-link was between the alpha chains. X-ray crystallographic studies of the modified hemoglobin were carried out to determine the exact site of cross-linking. FIG. 3 shows the difference electron density contour map between the cross-linked derivative and native deoxyhemoglobin superimposed upon the atomic model of the native structure. Contours due to negative difference electron density have been omitted for clarity. The band of positive difference electron density containing the two intense peaks near the center of the diagram is due to the cross-link bridge, which can be seen to connect lysine 99 (99K) of one alpha chain to lysine 99 of the second alpha chain. The other low level positive contours are due to small changes in the structure as a result of the cross-link. No other sites of modification were observed in the difference map.

EXAMPLE 2

New Protein Modifying Agents which Attach Negatively Charged Groups Within the 2,3-Diphosphoglycerate Binding Site This example first describes the reaction of mono(3,5dibromosalicyl) fumarate with native hemoglobin. The reaction of interest occurs with oxyhemoglobin, in which cases the compound reacts selectively at Lys 82 beta as shown in the following equation and introduces a negatively charged carboxylate group (underlined) within the DPG binding site:

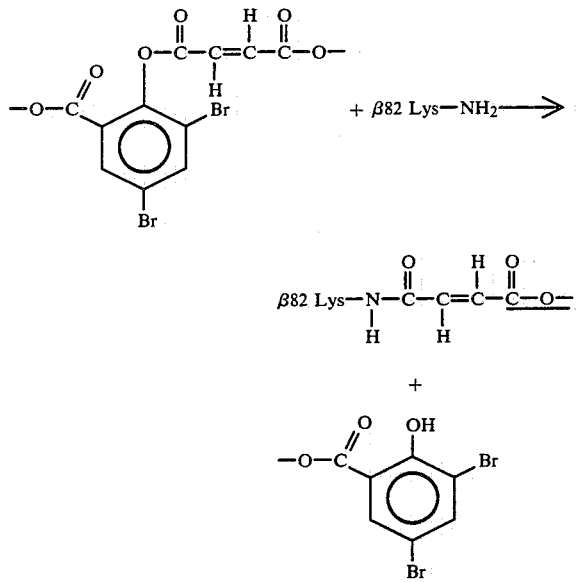

The reaction conditions are the same as described in Example 1, except that hemoglobin is maintained in the oxy form. Normal ambient partial pressures of oxygen in room air are sufficient for this purpose. With a 1.5 molar excess of the reagent over hemoglobin the yield of the product was approximately 20%. The derivative was purified by chromatography on DEAE cellulose as described in the previous example. Two-dimensional gel electrophoresis of the modified hemoglobin showed that both of the beta chains were modified. X-ray crystallographic studies showed that the site of modification was at Lys 82 of the beta chains. This was confirmed by tryptic peptide mapping. The oxygen affinity of the modified hemoglobin is decreased by approximately 1.6 fold. At a pH of 7.0 in 50 mM Bis-Tris buffer, the $P_{50}$ was found to be increased from 7.9 mmHg for native hemoglobin to 12.9 mmHg for the modified derivative.

The reaction of mono(3,5-dibromosalicyl) fumarate with the alpha-alpha cross-linked derivative described in Example 1 under oxygenated conditions, occurs similarly to native hemoglobin. Correspondingly, oxygen binding studies as those in FIG. 2 show that the oxygen affinity of the alpha-alpha cross-linked derivative is further decreased by the addition of the negatively charged carboxylate group within the DPG binding site. In principle, a number of different derivatives could be prepared, having a range of oxygen affinities, by modification of the alpha-alpha cross-linked derivative with analogs of mono(3,5-dibromosalicyl) fumarate. The resulting oxygen affinity will depend on the negatively charged group which is added within the DPG binding site. In the following general structure:

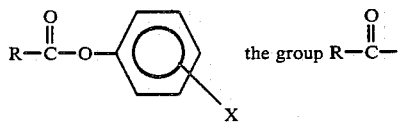

becomes covalently attached to the protein. The number and type of negatively charged substituents within this group may be varied. In addition to the carboxyl group these would include phosphonate, phosphate, sulfonate, and sulfate groups. In general, the greater the number of negative charges on the attached group, the lower would be the oxygen affinity of the modified hemoglobin.

In summary, the results of the studies performed demonstrate that the alpha-alpha intramolecularly cross-linked hemoglobin, described herein has the properties of an effective blood substitute, plasma expander and in general can be used for this purpose where conventional donor blood samples are now used.

Other modifications may be made without necessarily departing from the scope and spirit of the invention, the important factor and contribution being the discovery and use and technique for the alpha-alpha cross-linked modified hemoglobin.

It can further be seen that the invention accomplishes at least all of the objectives heretofore stated.

What is claimed is:

1. A pharmaceutical composition for use as a blood substitute and blood plasma expander comprising a therapeutically effective amount of Lys 99 Alpha$_1$ to Lys 99 Alpha$_2$ intramolecularly cross-linked, stroma-free hemoglobin, substantially free of hemoglobin modified at other sites, soluble in aqueous and physiological fluids and capable of reversibly binding oxygen, and a pharmaceutically acceptable carrier.

2. The composition of claim 1 wherein said alpha-alpha cross-link is with an amino group-specific cross-linking agent.

3. The composition of claim 2 wherein said cross-linking agent is an acylating agent.

4. The composition of claim 3 wherein said cross-linking agent is a diester cross-linking agent.

5. The composition of claim 6 wherein said cross-linking agent is a phenyl ester cross-linking agent.

6. The composition of claim 7 wherein said cross-linking agent is bis(3,5-dibromosalicyl) fumarate.

7. The composition of claim 1 wherein the carrier is liquid and the composition contains from about 1% to about 10% of said hemoglobin.

8. The composition of claim 1 wherein said hemoglobin is also modified with a second reagent introducing a negatively charged group at the 2,3-diphosphoglycerate binding site.

9. The composition of claim 8 wherein said reagent is mono(3,5-dibromosalicyl) fumarate.

10. A method of replacing or increasing the circulating blood volume or increasing oxygen delivery to tissues in man or animal species comprising:
transfusing into the blood circulatory system a blood volume expander which consists essentially of Lys 99 Alpha$_1$ to Lys 99 Alpha$_2$ intramolecularly cross-linked, stroma-free hemoglobin which is substantially free of hemoglobin derivatives modified at other sites, having a molecular weight of about 64,000 in an isotonic solution.

11. The method of claim 10 wherein the hemoglobin is also modified with a negatively charged group at the 2,3-diphosphoglycerate binding site.

* * * * *